(12) United States Patent
Konno et al.

(10) Patent No.: US 10,529,471 B2
(45) Date of Patent: Jan. 7, 2020

(54) DIELECTRIC MATERIAL

(71) Applicant: JAPAN SCIENCE AND TECHNOLOGY AGENCY, Kawaguchi-shi (JP)

(72) Inventors: Takumi Konno, Toyonaka (JP); Satoshi Yamashita, Toyonaka (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 16/334,140

(22) PCT Filed: Sep. 19, 2017

(86) PCT No.: PCT/JP2017/033629
§ 371 (c)(1),
(2) Date: Apr. 9, 2019

(87) PCT Pub. No.: WO2018/056237
PCT Pub. Date: Mar. 29, 2018

(65) Prior Publication Data
US 2019/0304635 A1    Oct. 3, 2019

(30) Foreign Application Priority Data

Sep. 20, 2016  (JP) .................................. 2016-182562

(51) Int. Cl.
*H01C 7/04* (2006.01)
*C07F 15/06* (2006.01)
(Continued)

(52) U.S. Cl.
CPC .......... *H01C 7/049* (2013.01); *C07F 15/065* (2013.01); *G01K 7/22* (2013.01); *H01L 41/18* (2013.01)

(58) Field of Classification Search
CPC ........ H01C 7/049; H01C 7/041; H01C 17/18; H01C 17/265; C07F 15/065; G01K 7/22
See application file for complete search history.

(56) References Cited

U.S. PATENT DOCUMENTS

| 10,305,052 B2 * | 5/2019 | Fukushima ............. C07C 43/21 |
| 2002/0150697 A1 * | 10/2002 | Swager .................. C08G 61/02 |
| | | 428/1.1 |

(Continued)

FOREIGN PATENT DOCUMENTS

| JP | 63-19775 A | 1/1988 |
| JP | 2012-240939 A | 12/2012 |

(Continued)

OTHER PUBLICATIONS

International Search Report dated Dec. 12, 2017 in PCT/JP2017/033629, 2 pages.

(Continued)

*Primary Examiner* — Kyung S Lee
(74) *Attorney, Agent, or Firm* — Oblon, McClelland, Maier & Neustadt, L.L.P.

(57) ABSTRACT

Provided are a novel dielectric material and a novel electrostrictive material. The dielectric material or electrostrictive material comprises a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closest packed structure.

21 Claims, 13 Drawing Sheets

(51) Int. Cl.
    *G01K 7/22*     (2006.01)
    *H01L 41/18*     (2006.01)

(56) References Cited

U.S. PATENT DOCUMENTS

2016/0005974 A1*   1/2016   Fukushima ............. C07C 43/21
                                                           257/29
2016/0284790 A1    9/2016   Shimoda et al.

FOREIGN PATENT DOCUMENTS

| JP | 2016-138056 A | 8/2016 |
| WO | WO 2014/125527 A1 | 8/2014 |
| WO | WO 2014/148336 A1 | 9/2014 |

OTHER PUBLICATIONS

"Piezo/Electrostrictive Materials" Journal of the Japan Society for Precision Engineering—53-5, 1987, pp. 686-688 (with partial English translation).

Raeeun Lee, et al., "Extraordinary Aggregation of Inorganic Anions in Chiral Metallosupramolecular Ionic Crystals" Bull. Chemical Society Japan, vol. 86, No. 8, 2013, pp. 908-920.

Raeeun Lee, et al., "Aggregation of Chiral Hexanuclear Complex-cations Into Cationic Metallosupramolecules with Concomitant Aggregation of Inorganic Counter-Anions Into Anionic Clusters" CrystEngComm, vol. 14, 2012, pp. 1936-1938.

* cited by examiner

[Figure 1]
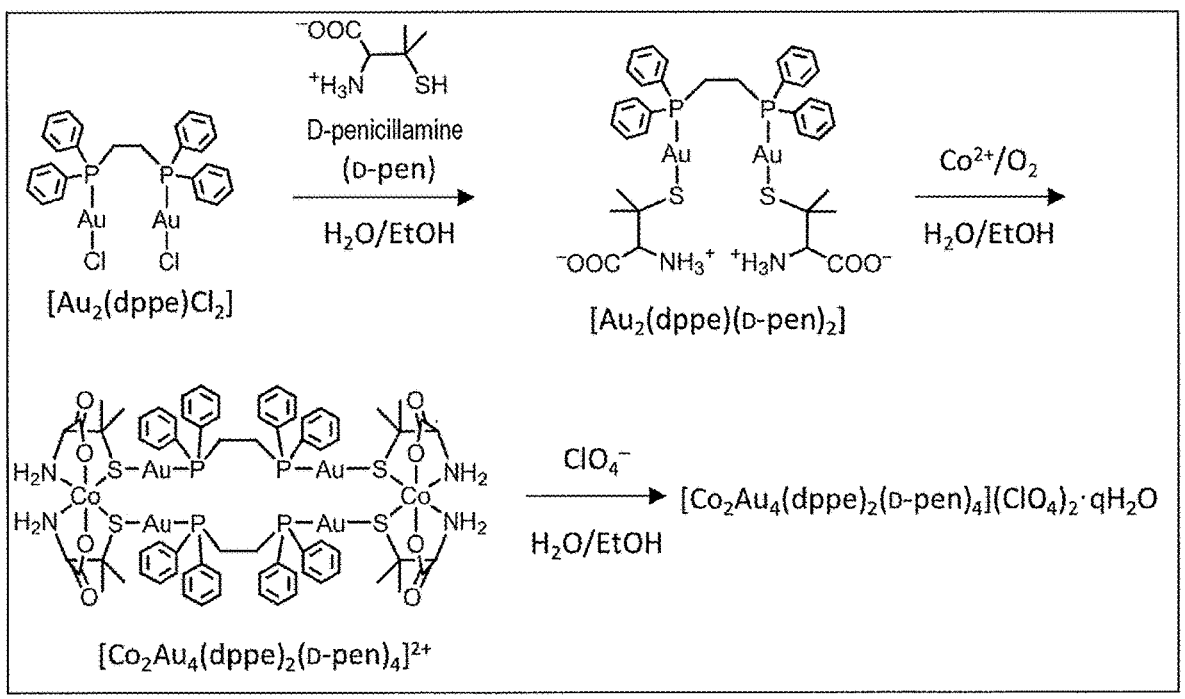

[Figure 2]
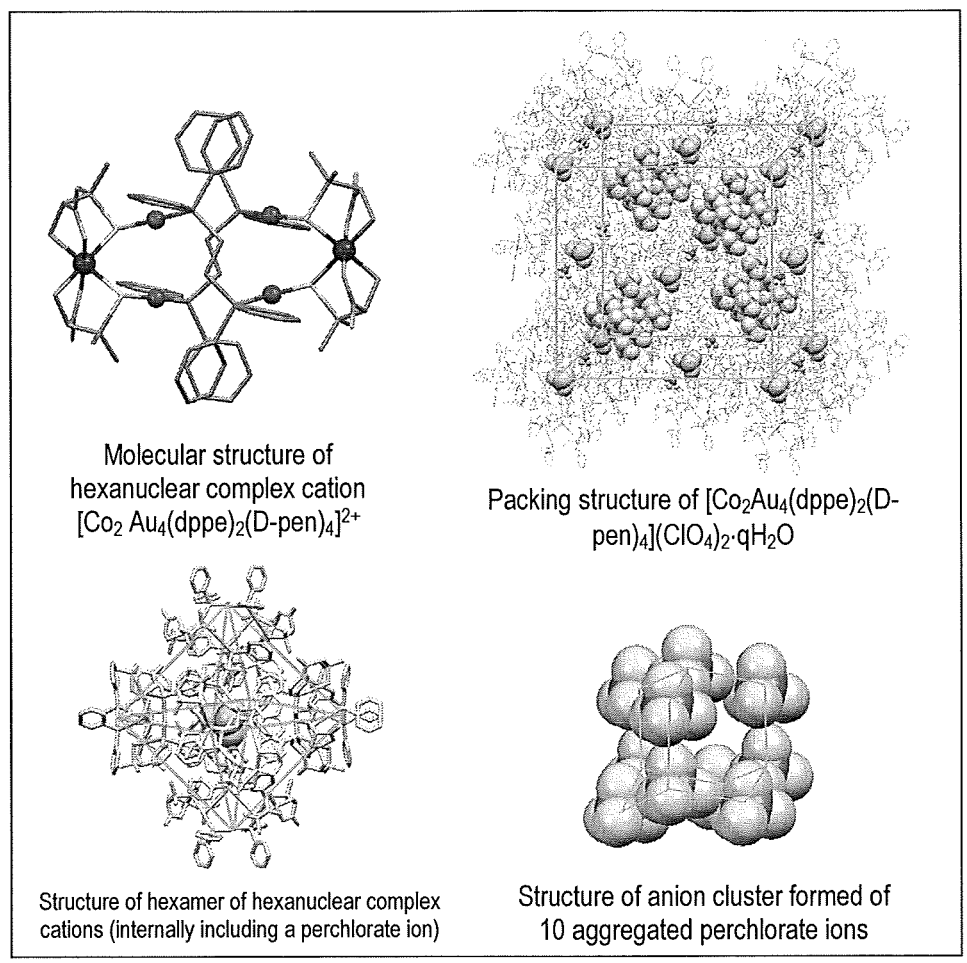

[Figure 3]
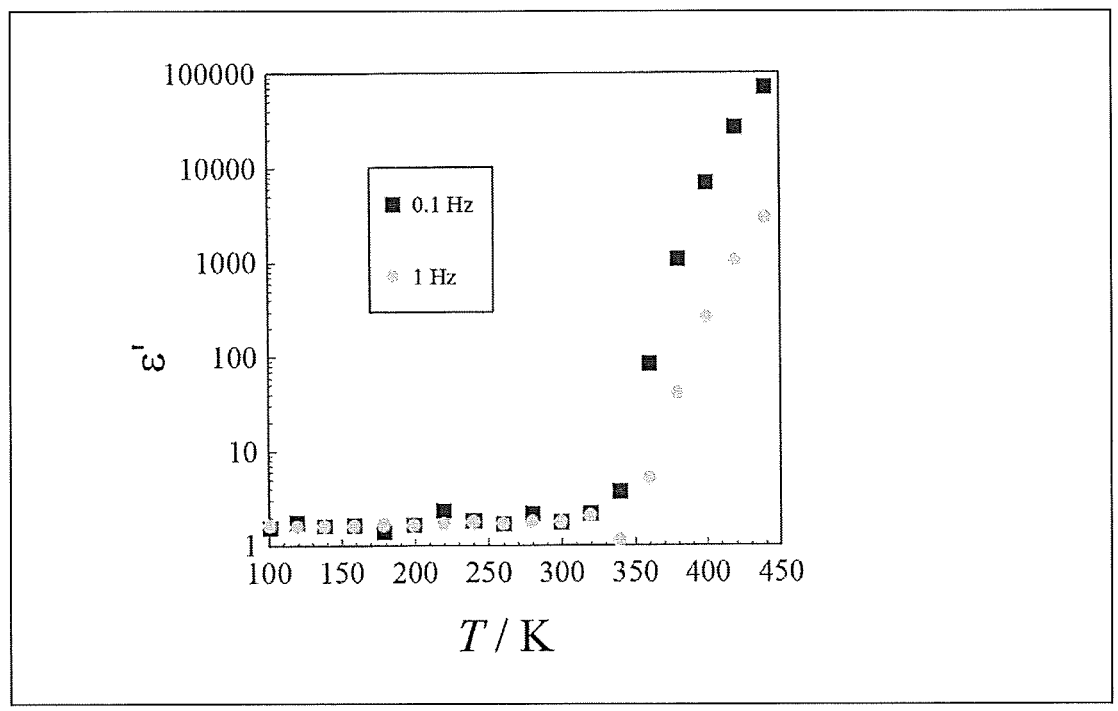

[Figure 4]
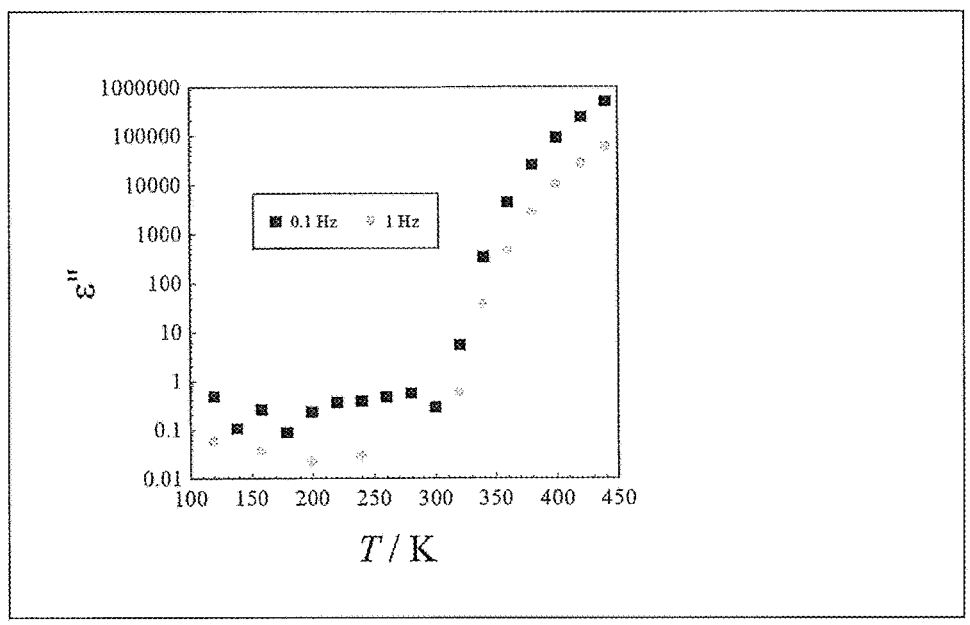

[Figure 5]
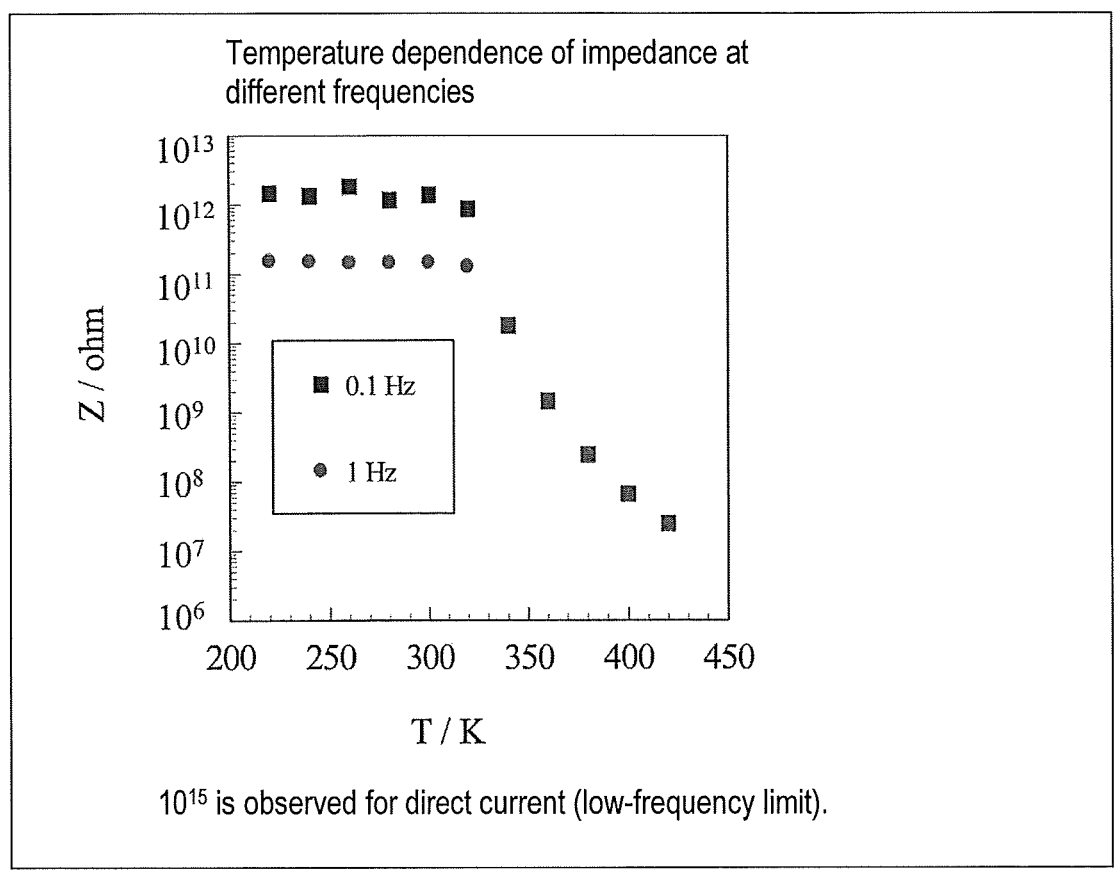

[Figure 6]
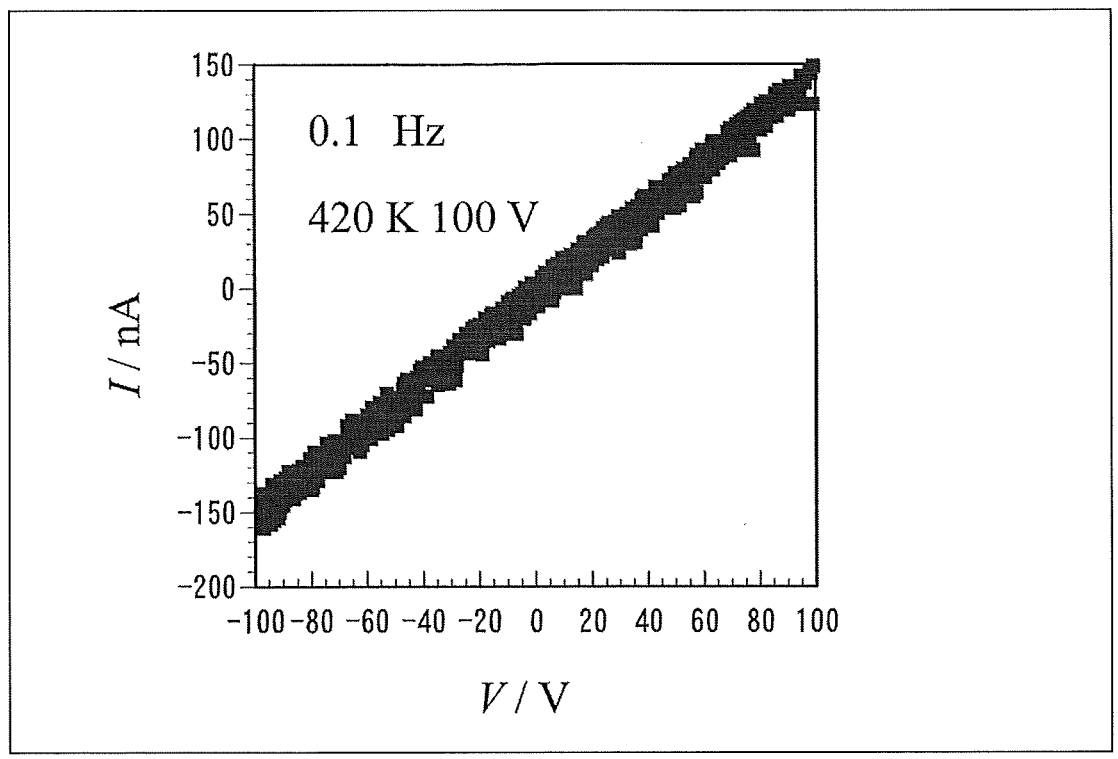

[Figure 7]
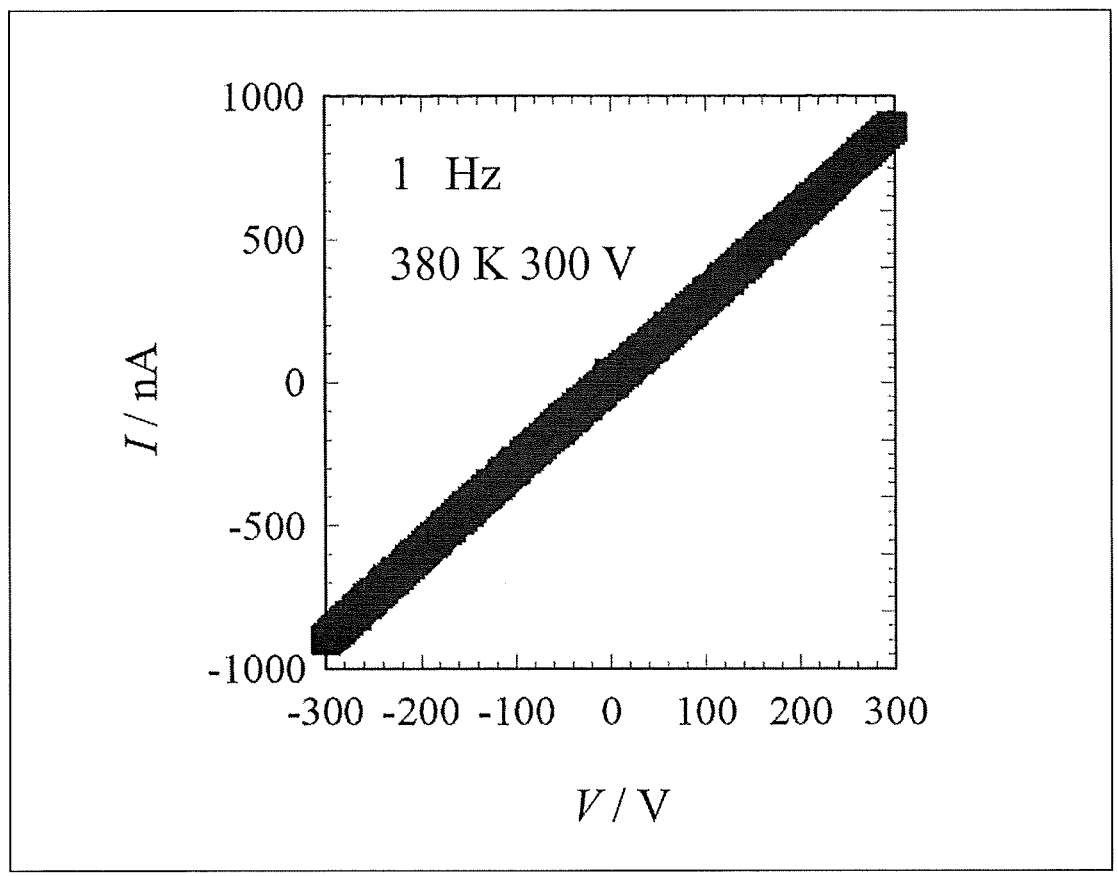

[Figure 8]
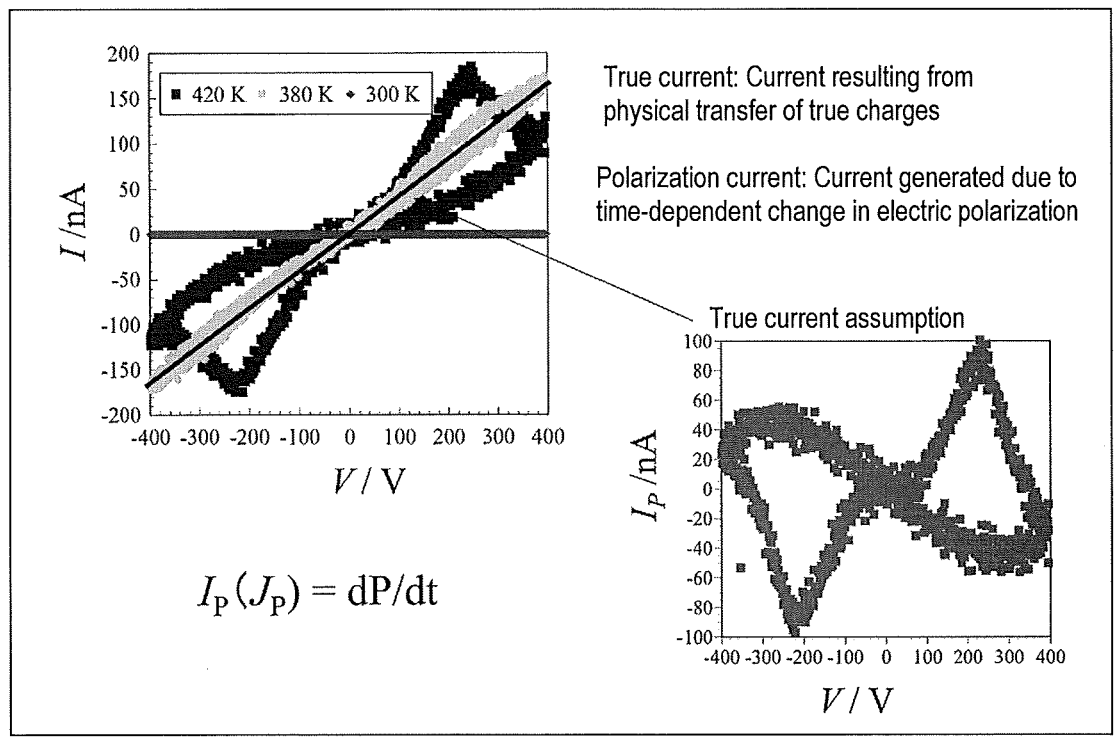

[Figure 9]
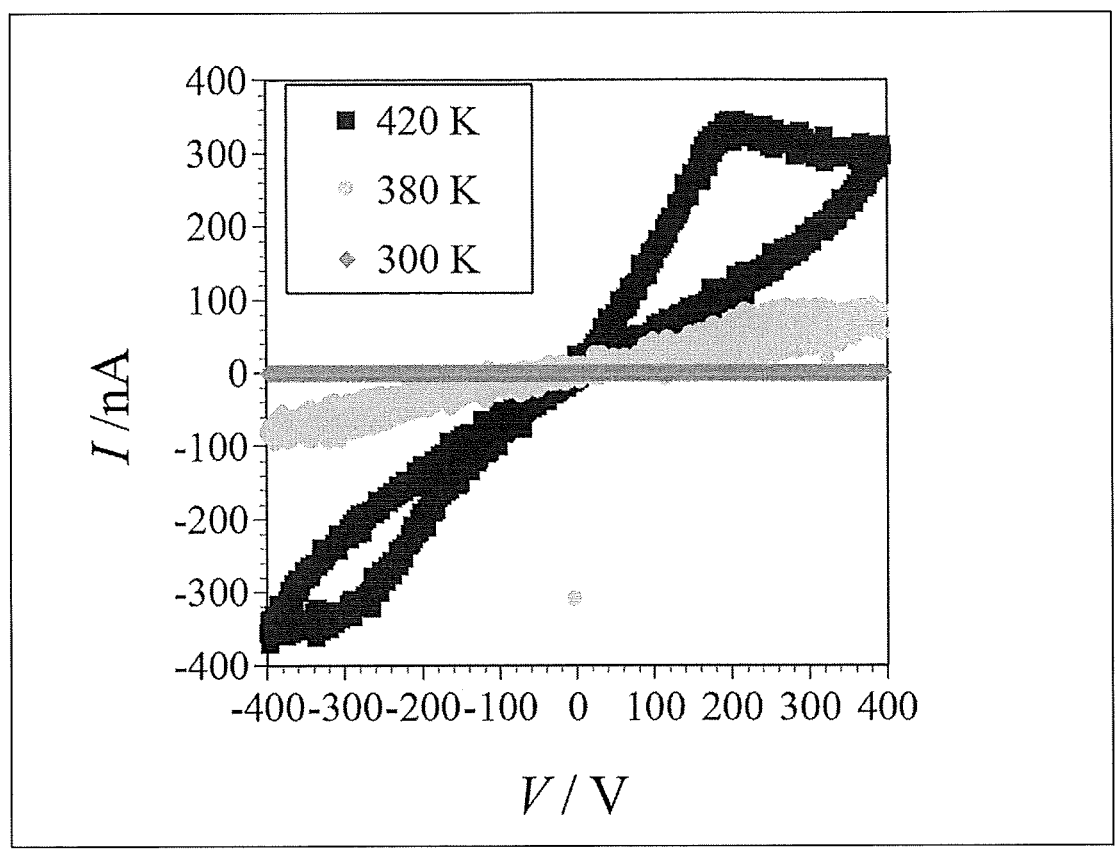

[Figure 10]
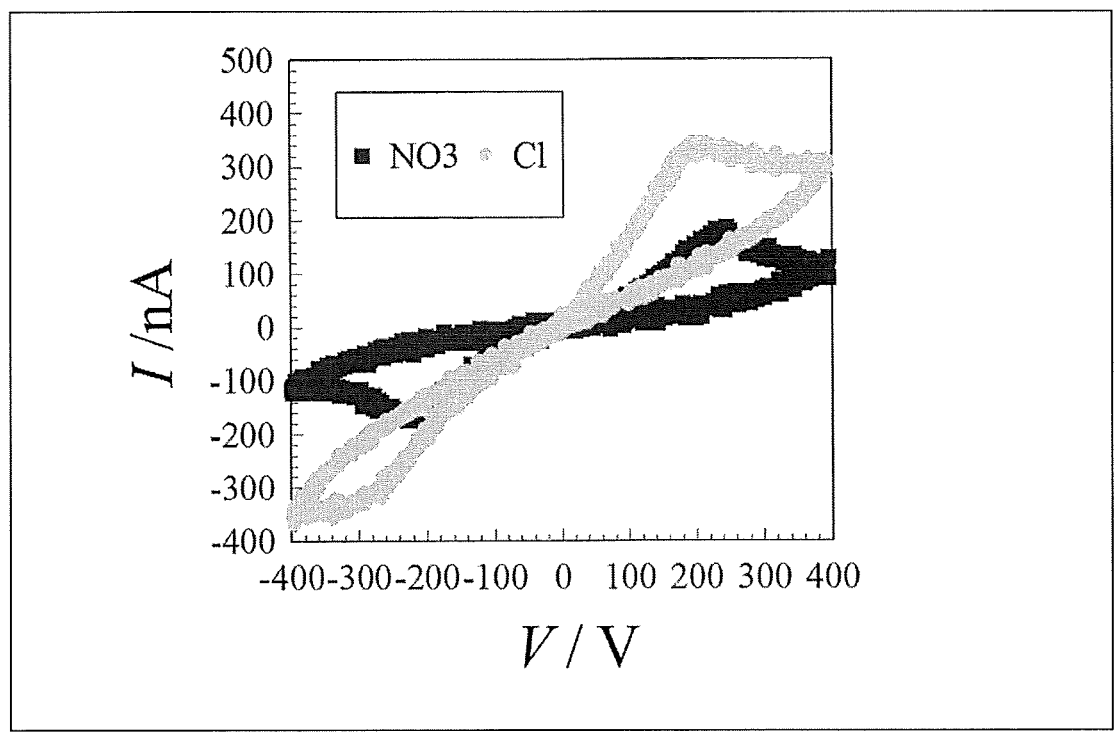

[Figure 11]
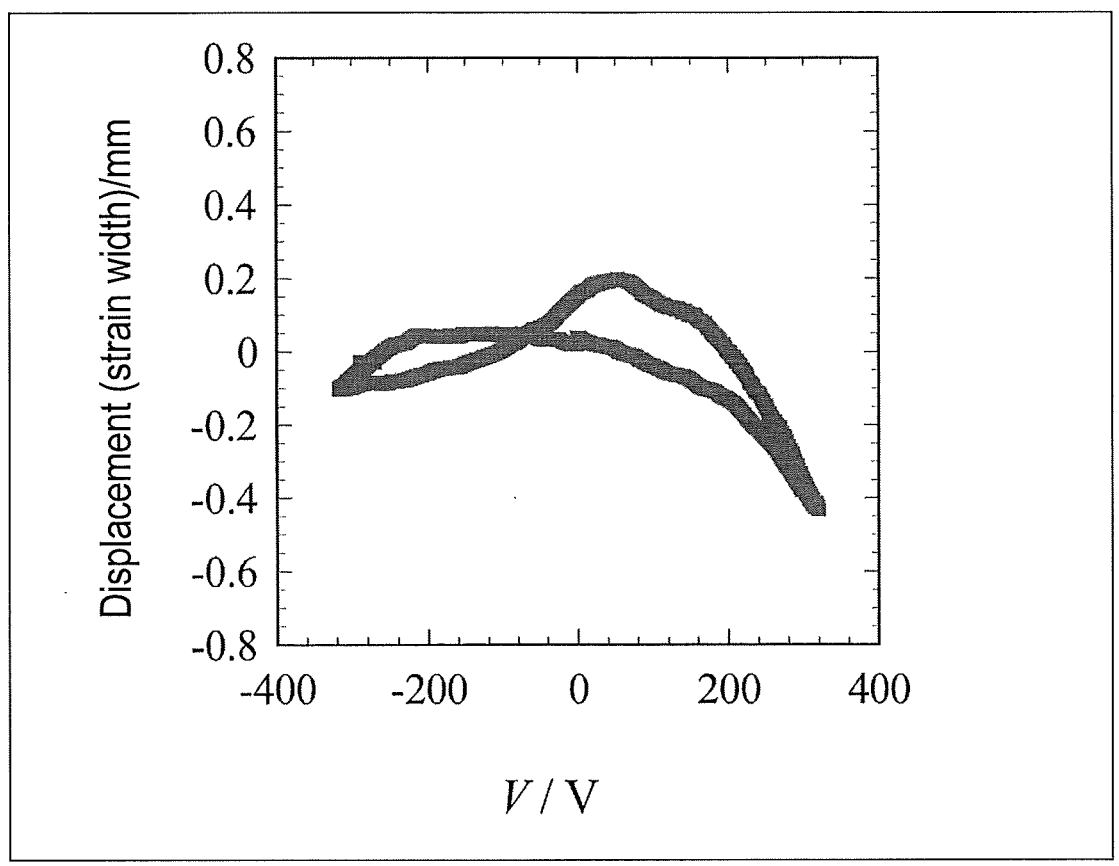

[Figure 12]
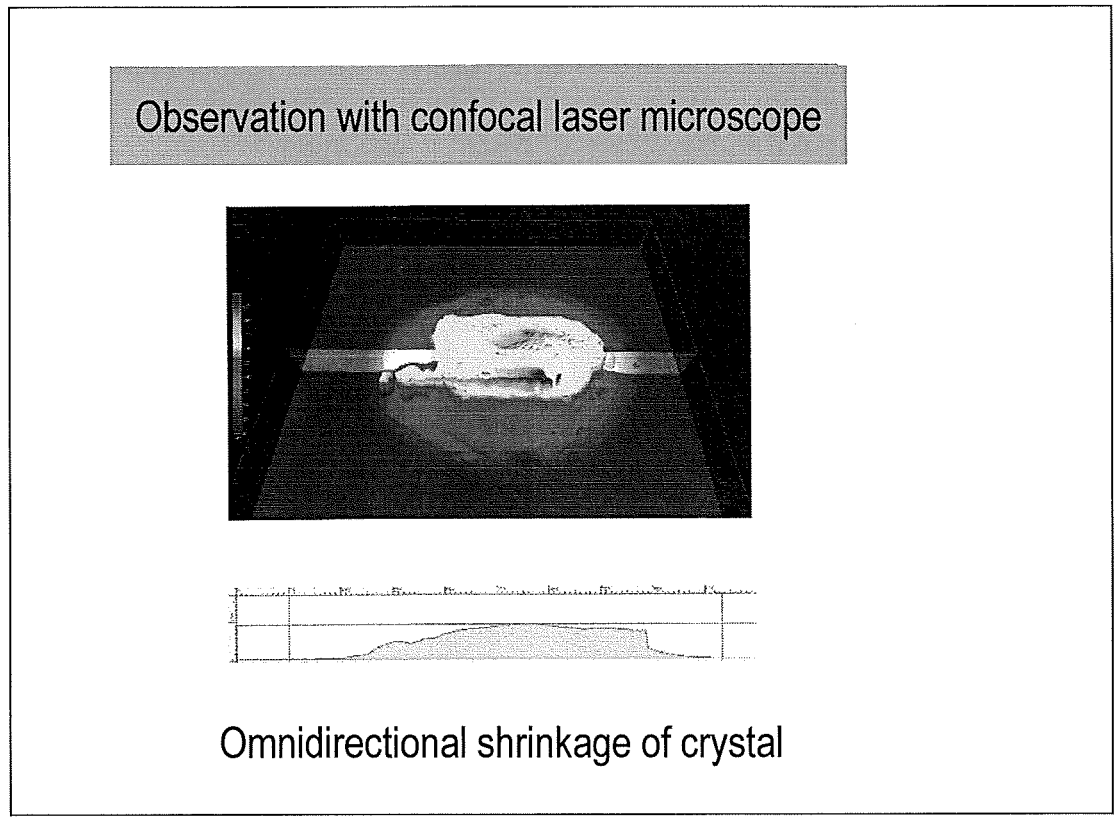
[Figure 13]
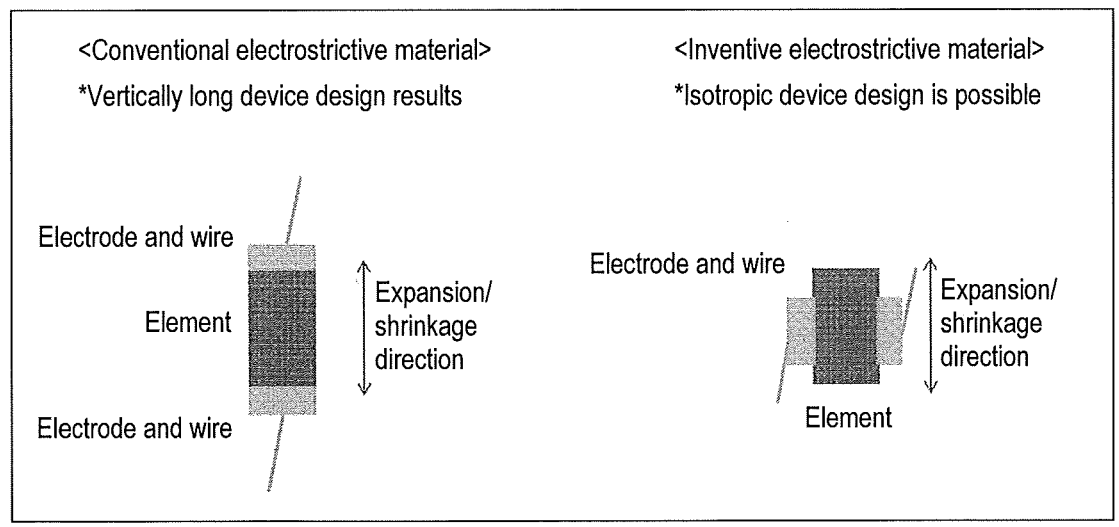

[Figure 14]
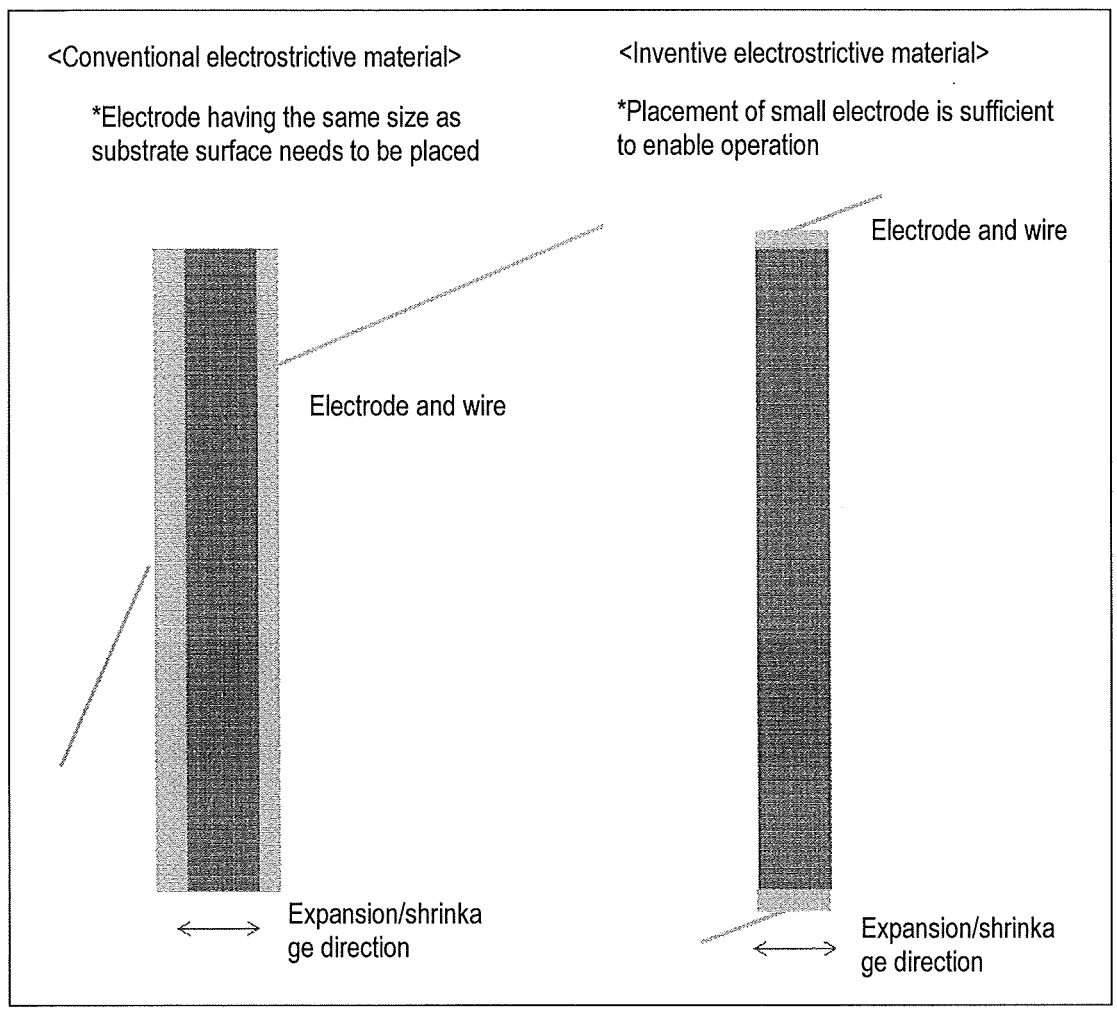

DIELECTRIC MATERIAL

TECHNICAL FIELD

The present invention relates to a novel dielectric material and a novel electrostrictive material.

BACKGROUND ART

Dielectrics are widely applied to capacitors, semiconductor devices, optical fibers, etc. For example, barium titanate, which has a perovskite structure, has a very high relative dielectric constant and is thus widely used as a dielectric material for multilayer ceramic capacitors.

Thermistors whose electrical resistance decreases with increasing temperature include NTC (negative temperature coefficient) thermistors whose electrical resistance slowly decreases with increasing temperature and CTR (critical temperature resistor) thermistors whose resistance abruptly drops once a certain temperature is exceeded. Sintered bodies of oxides of nickel, manganese, iron etc. are used as NTC thermistors. Sintered bodies produced by sintering an oxide of vanadium with an additive are used as CTR thermistors.

However, NTC thermistors have limited applications because the decrease in electrical resistance with increasing temperature is slow. Currently used CTR thermistors generally lack a sufficiently high initial electrical resistance value and are available only in a small variety of types; hence, these CTR thermistors may fail to operate depending on the resistance value of a circuit, thus having a limited use. Additionally, for the CTR thermistors, the change in electrical resistivity with increasing temperature is on the order of $10^3$ times, and this causes problems such as low performance of a control circuit such as a thermostat. Further, when these thermistors are used as thermometers, there are the following problems: an NTC thermometer fails to perform sufficiently accurate temperature detection because of the slow decrease in electrical resistance of the NTC thermistor, whereas a CTR thermistor undergoes an abrupt resistance change in a narrow temperature region and thus has markedly reduced sensitivity as a thermometer outside a specific temperature region.

Piezoelectric materials, which are a class of dielectric materials, are inverse piezoelectric-type electrostrictive materials which experience strain upon application of electric field, and are widely used, for example, in actuators based on electrical-mechanical energy conversion. For example, lead zirconate titanate (PZT) is used as such an electrostrictive material (Non Patent Literature 1). In the case of typical already-developed electrostrictive materials, including those of the inverse piezoelectric type, the voltage application direction and the actuation direction are the same, and means such as a gear needs to be incorporated in order to enable operation in any other direction.

The present inventors conducted various investigations in an attempt to produce an ionic solid having an absolutely new function and have successfully created $[Au_4Co_2(dppe)_2(D\text{-}pen)_4](ClO_4)_2 \cdot qH_2O$. This ionic solid has been found to be a charge-separated ionic solid which, unlike naturally occurring ionic solids consisting of pairs of ions, is formed of ionic clusters and is held in a solid state by non-coulombic force (Non Patent Literature 2).

CITATION LIST

Non Patent Literature

Non Patent Literature 1: Journal of the Japan Society for Precision Engineering, 53/5/1987, p 686-688

Non Patent Literature 2: Bull. Chem. Soc. Jpn., 2013, 86, 908-920, CrystEngComm, 2012, 14, 1936-1938

SUMMARY OF INVENTION

Technical Problem

Conventional dielectric materials and electrostrictive materials have disadvantages such as low initial electrical resistance value, small change in electrical resistance, a extremely narrow temperature region over which the electrical resistance shows a significant change, small mechanical change, and limitation to the operation direction. Thus, the development of superior dielectric materials and electrostrictive materials has been desired.

It is therefore an object of the present invention to provide a novel dielectric material and a novel electrostrictive material.

Solution to Problem

The present inventors conducted various investigations as to the properties and applications of the above-mentioned charge-separated ionic solid about the function of which little has been known. As a result, the present inventors have found the ionic solid to be a superior dielectric material that has a quite excellent property of exhibiting a considerably large change in dielectric constant over the range from 100 K to 450 K, having a considerably high electrical resistivity at low temperature, and, in particular, exhibiting a decrease in electrical resistivity to as low as $1/100{,}000$ or less over the range from around room temperature to about 400 to 450 K. The present inventors have further found that this ionic solid has the following excellent electrostrictive property: its crystal isotropically shrinks as a whole upon voltage application, unlike conventional electrostrictive materials whose crystal, upon voltage application, expands in the voltage application direction and shrinks only in a direction orthogonal to the voltage application direction under the Poisson effect caused by the expansion in the voltage application direction. The present invention has been completed based on these findings.

Thus, the present invention provides the following [1] to [21].

[1] A dielectric material comprising a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closet packed structure.

[2] The dielectric material according to [1], wherein the charge-separation type non-coulombic ionic solid is a charge-separation type non-coulombic ionic solid in which multinuclear complex cations each composed of two metal elements and two ligands are aggregated to form cation clusters, the cation clusters are arranged in a face-centered cube, and inorganic anions serving as counter anions are aggregated to form anion clusters in tetrahedral interstices of the face-centered cube.

[3] The dielectric material according to [1] or [2], wherein the cation cluster is an $M^1M^2$ hexa- to deca-nuclear complex cation cluster in which an element ($M^1$) selected from the group consisting of elements of Group 10 and Group 11 and an element ($M^2$) selected from the group consisting of elements of Group 6, Group 9, and Group 13 are linked via two ligands ($X^1$ and $X^2$).

[4] The dielectric material according to any one of [1] to [3], wherein the charge-separation type non-coulombic ionic solid is a charge-separation type non-coulombic ionic solid represented by formula (1):

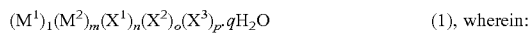  (1), wherein:

M¹ represents an element selected from the group consisting of elements of Group 10 and Group 11;

M² represents an element selected from the group consisting of elements of Group 6, Group 9, and Group 13;

X¹ represents a ligand having at least two phosphino groups;

X² represents a ligand having at least one thiol group and at least one carboxyl group;

X³ represents an anion;

l and m each represent a number from 2 to 6, wherein the sum of the numbers is 6 to 10; and n represents a number from 1 to 2, o represents a number from 2 to 6, and p and q each represent a number from 1 to 16.

[5] The dielectric material according to [3] or [4], wherein X¹ is a ligand having at least two diarylphosphino groups.

[6] The dielectric material according to any one of [3] to [5], wherein X² is a ligand having a hydrogen-bonding functional group in addition to a thiol group and a carboxyl group.

[7] The dielectric material according to any one of [1] to [6], wherein the charge-separation type non-coulombic ionic solid undergoes a decrease in electrical resistance value to 1/100,000 or less with a temperature change from 100 K to 450 K.

[8] A thermometer using the dielectric material according to any one of [1] to [7].

[9] A thermistor using the dielectric material according to any one of [1] to [7].

[10] A device protection circuit configured to operate in response to temperature increase, the device protection circuit comprising a thermostat using the dielectric material according to any one of [1] to [7].

[11] An electrostrictive material comprising a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closest packed structure.

[12] The electrostrictive material according to [11], wherein the charge-separation type non-coulombic ionic solid is a charge-separation type non-coulombic ionic solid in which multinuclear complex cations each composed of two metal elements and two ligands are aggregated to form cation clusters, the cation clusters are arranged in a face-centered cube, and inorganic anions serving as counter anions are aggregated to form anion clusters in tetrahedral interstices of the face-centered cube.

[13] The electrostrictive material according to [11] or [12], wherein the cation cluster is an M¹M² hexa- to decanuclear complex cation cluster in which an element (M¹) selected from the group consisting of elements of Group 10 and Group 11 and an element (M²) selected from the group consisting of elements of Group 6, Group 9, and Group 13 are linked via two ligands (X¹ and X²).

[14] The electrostrictive material according to any one of [11] to [13], wherein the charge-separation type non-coulombic ionic solid is a charge-separation type non-coulombic ionic solid represented by formula (1):

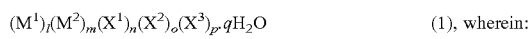  (1), wherein:

M¹ represents an element selected from the group consisting of elements of Group 10 and Group 11;

M² represents an element selected from the group consisting of elements of Group 6, Group 9, and Group 13;

X¹ represents a ligand having at least two phosphino groups;

X² represents a ligand having at least one thiol group and at least one carboxyl group;

X³ represents an anion;

l and m each represent a number from 2 to 6, wherein the sum of the numbers is 6 to 10; and n represents a number from 1 to 2, o represents a number from 2 to 6, and p and q each represent a number from 1 to 16.

[15] The electrostrictive material according to any one of [11] to [14], wherein X¹ is a ligand having at least two diarylphosphino groups.

[16] The electrostrictive material according to any one of [11] to [15], wherein X² is a ligand having a hydrogen-bonding functional group in addition to a thiol group and a carboxyl group.

[17] The electrostrictive material according to any one of [11] to [16], wherein the charge-separation type non-coulombic ionic solid isotropically shrinks upon voltage application.

[18] An actuator comprising the electrostrictive material according to any one of [11] to [17].

[19] A multinuclear metal complex represented by formula (1a):

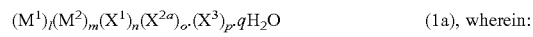  (1a), wherein:

M¹ represents an element selected from the group consisting of elements of Group 10 and Group 11;

M² represents an element selected from the group consisting of elements of Group 6, Group 9, and Group 13;

X¹ represents a ligand having at least two phosphino groups;

X²ᵃ represents a ligand having at least one thiol group and at least one carboxyl group, provided that the ligand is other than penicillamine;

X³ represents an anion;

l and m each represent a number from 2 to 6, wherein the sum of the numbers is 6 to 10; and n represents a number from 1 to 2, o represents a number from 3 to 6, and p and q each represent a number from 1 to 16.

[20] The multinuclear metal complex according to [19], wherein X¹ is a ligand having at least two diarylphosphino groups.

[21] The multinuclear metal complex according to [19] or [20], wherein X²ᵃ is a ligand having a hydrogen-bonding functional group in addition to a thiol group and a carboxyl group.

Advantageous Effects of Invention

The charge-separated ionic solid used in the dielectric material or electrostrictive material of the present invention exhibits a large change in dielectric constant over the temperature range from 100 K to 450 K and is useful as a dielectric material. The ionic solid has the property of, as a function of the dielectric constant change, exhibiting a large electrical resistance change such that the ratio of the electrical resistivity at 450 K (R(450 K)) to the resistivity at 100 K (R(100 K)), R(450 K)/R(100 K), is 1/10⁵ or less. The ionic solid is applicable, for example, to a device protection circuit configured to operate in response to temperature increase and comprising a thermostat, to a CTR thermistor, or to a thermometer.

The charge-separated ionic solid described above, utterly unlike conventional materials such as lead zirconate titanate, has the following property: its crystal isotropically shrinks as a whole upon voltage application. The ionic solid is useful as a new electrostrictive material and is applicable, for example, to an actuator.

Additionally, the charge-separated ionic solid represented by formula (1a) is a novel compound.

BRIEF DESCRIPTION OF DRAWINGS

FIG. 1 shows reactions in Example 1.

FIG. 2 shows the crystal structure of a charge-separated ionic solid obtained in Example 1.

FIG. 3 shows the change in dielectric constant of a charge-separated ionic solid.

FIG. 4 shows the change in dielectric loss component of a charge-separated ionic solid.

FIG. 5 shows the temperature dependence of the alternating-current impedance of a charge-separated ionic solid.

FIG. 6 shows the I-V characteristics of a charge-separated ionic solid.

FIG. 7 shows the I-V characteristics of a charge-separated ionic solid.

FIG. 8 shows the I-V characteristics of a charge-separated ionic solid.

FIG. 9 shows the I-V characteristics of a charge-separated ionic solid.

FIG. 10 shows the I-V characteristics of a charge-separated ionic solid.

FIG. 11 shows shrinkage of the crystal of a charge-separated ionic solid upon voltage application.

FIG. 12 shows omnidirectional shrinkage of the crystal of a charge-separated ionic solid.

FIG. 13 shows examples of device designs using electrostrictive substances.

FIG. 14 shows examples of electrode arrangements using electrostrictive substances.

DESCRIPTION OF EMBODIMENTS

A component used in the dielectric material or electrostrictive material of the present invention is a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closest packed structure. Hereinafter, this component may be referred to as "charge-separated ionic solid".

Conventionally known ionic solids can be called coulombic force-dominated solids because these solids are formed of cations and anions which are placed adjacent and close to each other and attracted to each other directly by a coulombic force to form bonded pairs, whereas the charge-separated ionic solid of the present invention is an ionic solid in which the cationic moieties and the anionic moieties form cation clusters and anion clusters, respectively, the positive and negative charges are separated from each other, and the solid formation is mainly due to a non-coulombic force.

The cation clusters are formed by accumulation of complex cations each composed of a metal element and a ligand. The complex cations can be obtained from a multinuclear organic complex compound composed of two metal elements and two ligands. The association state of the multinuclear organic complex compound used in the present invention can be varied by changing the types of the metal elements and ligands. Further, the complex cations in the present invention can be generated when anions as described below are selected. The complex cations in the present invention are aggregated to form cation clusters. As for the crystal structure, the cation clusters are arranged in a closest packed structure. The anions are aggregated to form anion clusters in interstices of the closet packed structure. Thus, the charge-separated ionic solid used in the present invention can be produced.

More preferred cation clusters are $M^1M^2$ hexa- to deca-nuclear complex cation clusters in which two elements ($M^1$) selected from the group consisting of elements of Group 10 and Group 11 and two elements ($M^2$) selected from the group consisting of elements of Group 6, Group 9, and Group 13 are linked via two ligands ($X^1$ and $X^2$). $X^1$ is preferably a ligand having at least two phosphino groups. $X^2$ is preferably a ligand having at least one thiol group and at least one carboxyl group.

Examples of the $M^1M^2$ hexa- to deca-nuclear complex include a complex represented by formula (A):

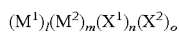
(A), wherein:

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^2$ represents a ligand having at least one thiol group and at least one carboxyl group;

l and m each represent a number from 2 to 6, wherein the sum of the numbers is 6 to 10; and n represents a number from 1 to 2, and o represents a number from 2 to 6.

In the charge-separated ionic solid, the cation clusters are arranged in a closest packed structure and are preferably arranged in a face-centered cube.

In the charge-separated ionic solid, the anion clusters are formed by accumulation of counter anions in the interstices formed as a result of the cation clusters being arranged in a closest packed structure. The anions are preferably inorganic anions. Preferably, the cation clusters are arranged in a face-centered cube, and the anion clusters are formed by accumulation of inorganic anions in the tetrahedral interstices of the face-centered cube.

FIG. 2 shows the molecular structure of an example of the $M^1M^2$ hexa- to deca-nuclear complex cation cluster ($[Au_4Co_2(dppe)_2(D\text{-pen})_4]^{2+}$: Example 1) in the charge-separated ionic solid of the present invention and also shows the cation clusters forming a face-centered cubic structure. It is seen that the $M^1M^2$ hexa- to deca-nuclear complex cation clusters form a face-centered cube. The anion clusters are included in the octahedral interstices of the face-centered cube.

Preferred examples of the charge-separated ionic solid used in the present invention include a charge-separation type non-coulombic ionic solid represented by the following formula (1):

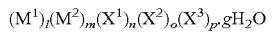
(1), wherein:

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^2$ represents a ligand having at least one thiol group and at least one carboxyl group;

$X^3$ represents an anion;

l and m each represent a number from 2 to 6, wherein the sum of the numbers is 6 to 10; and n represents a number from 1 to 2, o represents a number from 2 to 6, and p and q each represent a number from 1 to 16.

$M^1$ represents an element selected from the group consisting of elements of Group 10 and Group 11. Specific examples of $M^1$ include Au, Ag, Cu, Pt, Pd, and Ni, among which Au, Ag, and Cu are preferred, Au and Ag are more preferred, and Au is even more preferred.

$M^2$ represents an element selected from the group consisting of elements of Group 6, Group 9, and Group 13. Specific examples of $M^2$ include Co, Rh, Ir, Cr, Mo, W, B, Al, Ga, In, and Tl, among which Co, Cr, Ga, and In are preferred, Co and Cr are more preferred, and Co is even more preferred.

$X^1$ represents a ligand having at least two phosphino groups. Examples of such a phosphino group-containing ligand include ligands having two to four diarylphosphino groups as exemplified by a diphenylphosphino group. Examples of the ligand represented by $X^1$ include the following forms.

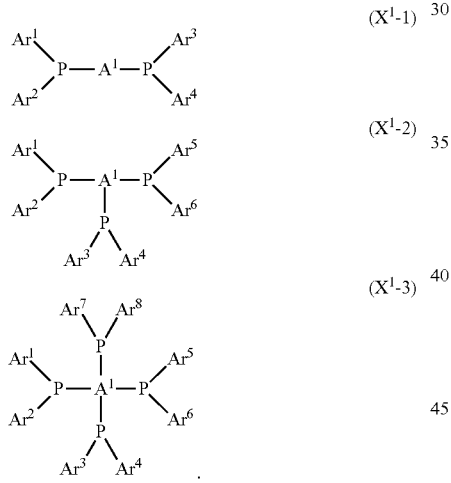

In the formulae, $Ar^1$ to $Ar^8$, which are the same or different, are each an aryl group, and $A^1$ is a linear or branched C1 to C10 alkylene or alkenylene group, a C6 to C24 arylene group, a C2 to C10 alkyleneaminoalkylene group, a C2 to C10 alkyleneoxyalkylene group, or a C2 to C10 alkylenethioalkylene group.

Examples of the aryl groups represented by $Ar^1$ to $Ar^8$ include C6 to C24 aryl groups, specific examples of which include phenyl, alkyl-substituted phenyl, and naphthyl groups. Examples of the C6 to C24 arylene group represented by $A^1$ include bisphenylene and bisnaphthylene. Examples of the C1 to C10 alkylene or alkenylene group include methylene, ethylene, propylene, trimethylene, butylene, tetramethylene, pentamethylene, hexamethylene, and vinylene groups. Examples of the C2 to C10 alkyleneaminoalkylene group include —$CH_2$—N($CH_3$)—$CH_2$—, —$(CH_2)_2$—N($CH_3$)—$(CH_2)_2$—, and —$(CH_2)_3$—N($CH_3$)—$(CH_2)_2$—. Examples of the C2 to C10 alkyleneoxyalkylene and alkylenethioalkylene groups include —$CH_2OCH_2$—, —$CH_2SCH_2$—, —$(CH_2)_2O(CH_2)_2$—, and —$(CH_2)_2S(CH_2)_2$—.

Specific examples of the ligand represented by $X^1$ include the following compounds.

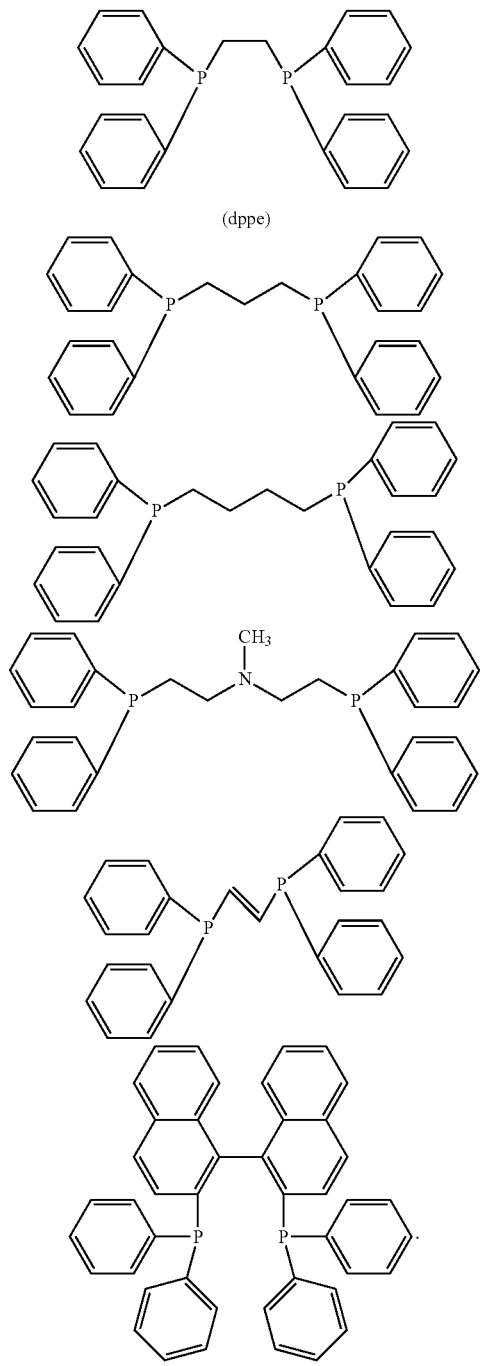

$X^2$ represents a ligand having at least one thiol group and at least one carboxyl group. The ligand represented by $X^2$ only has to be an organic compound having a thiol group and a carboxyl group and more preferably has a hydrogen-bonding functional group. Examples of the hydrogen-bonding functional group other than the thiol group and carboxyl group include amino, hydroxy, formyl, and alkylamino groups.

Examples of the ligand represented by $X^2$ include a thiol group-containing C2 to C18 carboxylic acid, a thiol group-containing C2 to C18 amino acid, and a thiol group-containing C2 to C18 hydroxy acid. Specific examples include cysteine, penicillamine (D-pen), N-methylcysteine, N-methylpenicillamine, N,N'-ethylenebiscysteine, and N,N'-ethylenebispenicillamine (D-epen).

$X^3$ represents an anion. The anion is not particularly limited and may include one or more selected from the group consisting of halogen ions, $N_3^-$, $NO_3^-$, $ClO_4^-$, $BF_4^-$, $SIF_6^{2-}$, $SO_4^{2-}$, $PF^-$, and $IO^{3-}$.

l and m each represent a number from 2 to 6, wherein the sum of the numbers is 6 to 10. For example, l is 2 and m is 4.

n represents a number from 1 to 2, o represents a number from 2 to 6, and p and q each represent a number from 1 to 16.

Preferred examples of the charge-separated ionic solid represented by formula (1) include $Au_2Co_4(X^1)_n(X^2)_o(X^3)_p \cdot qH_2O$, $Au_2Cr_4(X^1)_n(X^2)_o(X^3)_p \cdot qH_2O$, $Au_2Ga_4(X^1)_n(X^2)_o(X^3)_p \cdot qH_2O$, and $Au_2In_4(X^1)_n(X^2)_o(X^3)_p \cdot qH_2O$.

The charge-separated ionic solid used in the present invention can be obtained, for example, by reaction of a halide of $M^1$ with the ligand $X^1$, followed by reaction with the ligand $X^2$ and then by reaction with a halide of $M^2$.

The reaction of the ligand $X^1$ and a halide of $M^1$ can be carried out, for example, by stirring in an alcohol or halogen solvent. The subsequent reaction of the resulting compound and the ligand $X^2$ can be carried out by stirring in an alcohol/water mixed solvent in the presence of a base. The further reaction of the resulting compound and a halide of $M^2$ and the like can be carried out by stirring in an alcohol/water mixed solvent in the presence of a base.

As described in Non Patent Literature 2, the charge-separated ionic solid used in the present invention is a charge-separated ionic solid which, unlike naturally occurring ionic solids consisting of pairs of ions, is formed of ionic clusters and is held in a solid state due to non-coulombic force. However it has never been known that this charge-separated ionic solid has advantageous properties in terms of dielectric constant change and electrostriction. The present inventors have found that this charge-separated ionic solid is useful as a dielectric material, that the ionic solid has the property of, as a function of the dielectric constant change, exhibiting a considerable electrical resistance change such that the ratio of the electrical resistivity at 450 K (R(450 K)) to the electrical resistivity at 100 K (R(100 K)), R(450 K)/R(100 K), is $1/10^5$ or less, and that the ionic solid is applicable, for example, to a device protection circuit configured to operate in response to temperature increase and comprising a thermostat, to a thermometer, or to a thermistor.

The present inventors have further found the following facts: the charge-separated ionic solid, utterly unlike conventional materials such as lead zirconate titanate, has the following property: its crystal isotropically shrinks as a whole upon voltage application; the ionic solid thus allows operation in a direction different from the voltage application direction; and the ionic solid is therefore useful as a new electrostrictive material and applicable, for example, to an actuator.

Among charge-separated ionic solids represented by formula (1), the charge-separated ionic solid represented by formula (1a) is a novel substance that is not mentioned in Non Patent Literature 2.

$$(M^1)_1(M^2)_m(X^1)_n(X^{2a})_o(X^3)_p \cdot qH_2O \quad \text{(1a), wherein:}$$

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^{2a}$ represents a ligand having at least one thiol group and at least one carboxyl group, provided that the ligand is other than penicillamine;

$X^3$ represents an anion;

l and m each represent a number from 2 to 6, wherein the sum of the numbers is 6 to 10; and n represents a number from 1 to 2, o represents a number from 3 to 6, and p and q each represent a number from 1 to 16.

In formula (1a), $M^1$, $M^2$, $X^1$, $X^{2a}$, $X^3$, l, m, n, o, p, and q are the same as those defined in formula (1) above. Preferred examples of these elements and ligands are also the same as those mentioned for formula (1) above.

The charge-separated ionic solid used in the present invention exhibits a large dielectric constant change, in particular a dielectric constant change from $\varepsilon=2$ to $\varepsilon=$ about several tens of thousands, over the temperature range from 100 K to 450 K. The ionic solid further has the following property: as a function of the dielectric constant change, the alternating-current resistance (alternating-current impedance) of a single crystal of the solid with a size of about 0.7 mm×0.7 mm×0.5 mm greatly changes from several T ($10^{12}$) Ω to the order of 10 M ($10^7$) Ω with increasing temperature. In particular, the following property: the impedance value Z changes with a temperature change from 250 K to 450 K so that the ratio of the impedance value at 450 K (Z (450 K)) to the impedance value at 250 K (Z (250 K)), Z(450 K)/Z(250 K), is $1/10^5$ or less, or more particularly the electrical resistivity for direct-current resistance corresponding to the low-frequency limit of the alternating-current impedance decreases to $1/10^6$ to $1/10^8$, makes the charge-separated ionic solid significantly superior to existing dielectric materials in terms of temperature-dependent change in alternating-current impedance. The charge-separated ionic solid is superior to existing dielectric materials also in that the low-temperature electrical resistivity, which may correspond to the initial resistivity when the ionic solid is caused to act as a CTR thermistor, is considerably high.

In the charge-separated ionic solid used in the present invention, anion clusters containing water molecules (2 to 16 water molecules) are present in a crystal lattice formed by cations. A possible reason for the large temperature-dependent change in dielectric constant is that, under electric field, the anions and water molecules of the clusters undergo displacement and orientation change in the crystal in conjunction with lattice vibration.

Examples of temperature sensors and thermostats using the charge-separated ionic solid include thermometers and thermostats incorporating the charge-separated ionic solid (1) as a dielectric, resistor, or CTR thermistor. For the charge-separated ionic solid, as can be calculated from the resistance value shown in FIG. 5 for a crystal with a cross-sectional area of 0.7 mm×0.7 mm and a thickness of 0.5 mm, the value of the alternating-current impedance or effective resistivity at 0.1 Hz (1 V/mm) is about $10^{15}$ Ω/m (about $10^{16}$ to $10^{18}$ Ω/m at 0.01 Hz, 100 V/mm) at room temperature and abruptly decreases to about $10^{10}$ Ω/m at 450 K. This change is continuous with respect to temperature and cannot be explained based on the phase-transition behavior, thus indicating that the charge-separated ionic solid can adapt to various temperatures. The charge-separated ionic solid is useful as a CTR thermistor due to the property of exhibiting an abrupt decrease in resistivity, and can also be used for a circuit aimed at energy saving based on increase in circuit electrical resistance value since the charge-separated ionic solid exhibits a very high resistivity at low temperature and at around room temperature.

The above-described temperature-dependent change in electrical resistivity can be exploited in an ultrasensitive thermometer applicable to a wide temperature range including room temperature and, in addition, the repeatability of such a change is so high that this property can be exploited in an ultrahigh-resistance, ultrasensitive thermometer for control of an electronic device and the like.

A device protection circuit configured to operate in response to temperature increase and comprising a thermostat using the charge-separated ionic solid can be adjusted to have a resistivity of $10^{15}$ Ω/m or more at 25° C. or lower and a resistivity of $10^{10}$ Ω/m or less at 100° C. or higher, for example, with the use of a circuit incorporating the charge-separated ionic solid, and such a protection circuit can protect devices against temperature change.

Upon voltage application to a crystal of the charge-separated ionic solid at about 100 v/mm, the whole crystal isotropically shrinks. The shrinkage ratio is as high as 0.07%. This shrinkage ratio attributed to the electrostrictive property of the solid is considerably higher than 0.02 to 0.04%, which corresponds to the shrinkage ratio of lead zirconate titanate ($PbZr(TiO_4)$) which has been widely used. Existing electrostrictive materials expand in the direction of the applied electric field and, due to the Poisson effect, slightly shrink in a direction orthogonal to the applied electric field, whereas the electrostrictive material of the present invention has the property of isotropically shrinking in all directions upon application of electric field. The property of isotropically shrinking in all directions allows great flexibility in determining the directions in which electrodes or wires extend and is therefore advantageous for device design (see FIGS. 13 and 14, for example). The property of volume shrinkage is not possessed by any other dielectric materials, and enables the operation direction to be set without the aid of, for example, an actuator. The properties described above make it possible to broaden the range of applications of electrically-driven, expanding/shrinking elements as exemplified by piezoelectric elements and offer technology which helps in design and size reduction of devices.

The charge-separated ionic solid used in the present invention is in the form of a crystal having an isotropic cubic lattice. In this crystal, the cation clusters are arranged in a face-centered cube, and anion clusters containing water molecules (2 to 16 water molecules) are present in the interstices of the face-centered cube. A possible reason for the isotropic volume shrinkage is that the anions and water molecules of the clusters undergo displacement and orientation change in response to electric field.

An actuator using the charge-separated ionic solid is an actuator exploiting the charge-separated ionic solid as an electrostrictive material that shrinks upon voltage application. Specifically, the actuator can be in the form of a monomorph actuator, a bimorph actuator, a multilayer actuator, or the like, and can be used, for example, as a driving element for an atomic force microscope (AFM).

EXAMPLES

Hereinafter, the present invention will be described in detail with reference to examples. The present invention is not limited to the examples in any respect.

Example 1 (Synthesis of $Au_4Co_2(dppe)_2(D\text{-pen})_4(ClO_4)_2 \cdot qH_2O$)

(1) (Synthesis)

1 g of $[(AuCl)_2(dppe)]$ was suspended in 120 mL of ethanol, and to the suspension was added a solution prepared by dissolving 0.36 g of D-penicillamine (D-pen) in 24 mL of a 0.1 M aqueous KOH solution. The resulting mixture was stirred at room temperature for two hours to obtain a colorless solution. This solution was concentrated to dryness, and the dried residue was dissolved in an ethanol/water (1:1) mixed solvent. The solution was naturally concentrated for several days to obtain $[Au_2(dppe)(D\text{-pen})_2] \cdot 8H_2O$ as a colorless crystal. The isolated yield was 80%.

Next, 50 mg of $[Au_2(dppe)(D\text{-pen})_2] \cdot 8H_2O$ was dissolved in 6 mL of an ethanol/water (1:1) mixed solvent, and 10 mg of cobalt(II) acetate and 100 mg of lead(IV) oxide were added to the solution, which was stirred in water for 2 hours. The resulting reaction mixture was filtered to remove the unreacted lead(IV) oxide, and to the filtrate was added 1.2 mL of a 0.1 M aqueous sodium perchlorate solution. The resulting solution was naturally concentrated at room temperature for several days to obtain a target substance as a purple crystal (FIG. 1). The isolated yield was 92%.

(2) Analysis of Crystal Structure

A good crystal as obtained in (1) was subjected to single crystal X-ray diffraction using R-AXIS-RAPID manufactured by Rigaku Corporation. In the crystal, there was formed a dinuclear gold complex unit ($[Au_2(dppe)(D\text{-pen})_2]^{2-}$) having a structure in which two $[Au(D\text{-pen})]^-$ units each having the D-pen ligand with its sulfur atom linked to a gold ion were cross-linked with the diphosphine ligand dppe. Additionally, two such dinuclear gold complex units were cross-linked, via the D-pen moieties, with two octahedral cobalt (III) ions to form a hexanuclear $Au_4Co_2$ complex cation ($[Au_4Co_2(dppe)_2(D\text{-pen})_4]^{2+}$). The hexanuclear complex cations formed a hexamer (FIG. 2) through intermolecular NH—O hydrogen bonds and CH-π interaction. The cationic hexamer included one perchlorate ion at the center of the hexamer. It was also observed that the cationic hexamers were arranged in a face-centered cubic structure and that the face-centered cubic structure included an anion cluster consisting of 10 aggregated perchlorate ions in the tetrahedral interstice and one perchlorate ion in the octahedral interstice. The inside of the anion cluster and the other spaces present in the crystal were filled with water molecules.

Example 2

Synthesis of Various Anion-Addition Products of $Au_4Co_2(dppe)_2(D\text{-pen})_4$ The following charge-separated ionic solids were synthesized in the same manner as in Example 1, except that aqueous solutions of sodium salts of various anions were used instead of the aqueous sodium perchlorate solution $Au_4Co_2(dppe)_2(D\text{-pen})_4Cl_2 \cdot gH_2O$ $Au_4Co_2(dppe)_2(D\text{-pen})_4Br_2 \cdot qH_2O$ $Au_4Co_2(dppe)_2(D\text{-pen})_4(N_3)_2 \cdot qH_2O$

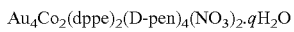
Au$_4$Co$_2$(dppe)$_2$(D-pen)$_4$(NO$_3$)$_2$·qH$_2$O

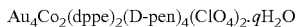
Au$_4$Co$_2$(dppe)$_2$(D-pen)$_4$(ClO$_4$)$_2$·qH$_2$O

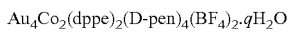
Au$_4$Co$_2$(dppe)$_2$(D-pen)$_4$(BF$_4$)$_2$·qH$_2$O

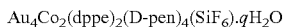
Au$_4$Co$_2$(dppe)$_2$(D-pen)$_4$(SiF$_6$)·qH$_2$O

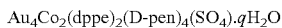
Au$_4$Co$_2$(dppe)$_2$(D-pen)$_4$(SO$_4$)·qH$_2$O

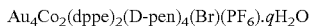
Au$_4$Co$_2$(dppe)$_2$(D-pen)$_4$(Br)(PF$_6$)·qH$_2$O

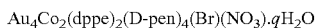
Au$_4$Co$_2$(dppe)$_2$(D-pen)$_4$(Br)(NO$_3$)·qH$_2$O

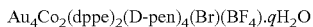
Au$_4$Co$_2$(dppe)$_2$(D-pen)$_4$(Br)(BF$_4$)·qH$_2$O

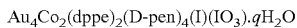
Au$_4$Co$_2$(dppe)$_2$(D-pen)$_4$(I)(IO$_3$)·qH$_2$O

Example 3

The following charge-separated ionic solids were synthesized in the same manner as in Example 1, except that Co was replaced by Cr or Ga.

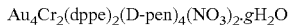
Au$_4$Cr$_2$(dppe)$_2$(D-pen)$_4$(NO$_3$)$_2$·gH$_2$O

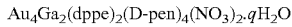
Au$_4$Ga$_2$(dppe)$_2$(D-pen)$_4$(NO$_3$)$_2$·qH$_2$O

Example 4

A charge-separated ionic solid was synthesized in the same manner as in Example 1, except that the following compound was used instead of 1,2-bis(diphenylphosphino)ethane (dppe).

Example 5

A charge-separated ionic solid was synthesized in the same manner as in Example 1, except that D-penicillamine (D-pen) was replaced by N,N'-ethylenebispenicillamine (D-epen).

Example 6

Charge-separated ionic solids were synthesized in the same manner as in Example 5, except that the following compounds were used.

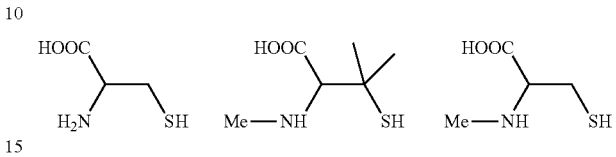

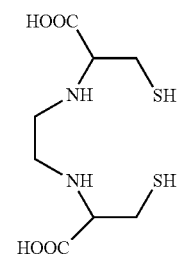

Parameters indicating the molecular structure of the ionic solids synthesized in Example 1 and Example 5 are listed in Table 1.

TABLE 1

| | Size of cation cluster (/Å) | Number of aggregated cations | Number of constituent atoms of cation | Number of constituent atoms of cation cluster | Size of anion cluster (/Å) | Number of aggregated anions | Number of constituent atoms of anion | Number of constituent atoms of anion cluster | Total atom number density (excluding water) (atoms/cm$^3$) |
|---|---|---|---|---|---|---|---|---|---|
| [1]Cl$_2$ | 33.3 | 6 | 182 | 1092 | 11.8 | 10 | 1 | 10 | 8.2 × 10$^{22}$ |
| [1](ClO$_4$)$_2$ | 32.7 | 6 | 182 | 1092 | 12.2 | 10 | 5 | 50 | 8.7 × 10$^{22}$ |
| [1](NO$_3$)$_2$ | 33.2 | 6 | 182 | 1092 | 13.7 | 10 | 4 | 40 | 8.3 × 10$^{22}$ |
| [1](SO$_4$) | 33.2 | 6 | 182 | 1092 | 11.1 | 6 | 5 | 30 | 8.2 × 10$^{22}$ |
| [2](NO$_3$)$_2$ | 34.1 | 6 | 190 | 1140 | 11.8 | 6 | 4 | 24 | 8.4 × 10$^{22}$ |
| [2]Cl$_2$ | 33.3 | 6 | 190 | 1140 | 10.8 | 6 | 1 | 6 | 8.4 × 10$^{22}$ |

[1]$^{2+}$ = [Au$_4$Co$_2$(dppe)$_2$(d-pen)$_4$]$^{2+}$
[2]$^{2+}$ = [Au$_4$Co$_2$(dppe)$_2$(d-epen)$_2$]$^{2+}$

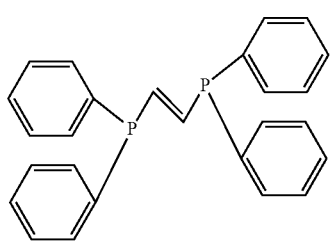 [SMILES: C(=C\P(c1ccccc1)c1ccccc1)/P(c1ccccc1)c1ccccc1]

Table 1 reveals that for the charge-separated ionic solid (M$^1$M$^2$ hexa- to deca-nuclear complex) used in the present invention, the size of the cation cluster is 30 Å to 35 Å, the number of the aggregated cations is 6, the number of constituent atoms of the cation is 182 to 190, the number of constituent atoms of the cation cluster is 1092 to 1140, the size of the anion cluster is 10 Å to 15 Å, the number of the aggregated anions is 6 to 10, the number of constituent atoms of the anion is 1 to 5, and the number of constituent atoms of the anion cluster is 6 to 50. The total atom number density (excluding water) was 8×10$^{22}$ to 9×10$^{22}$ atoms/cm$^3$.

The size of the cation cluster and the size of the anion cluster were determined by measuring the distance between the cations farthest from each other in the cation cluster and the distance between the anions farthest from each other in the anion cluster. The number of the aggregated cations refers to the number of aggregated metal atoms of the complex cation, while the number of the aggregated anions refers to the number of the aggregated anions themselves.

Example 7

(1) Changes in Dielectric Constant and Alternating-Current Impedance
(Method)

An electrode was formed with a graphite paste on a single crystal of charge-separated ionic solid with a cross-sectional area of about 0.7 mm×0.7 mm and a thickness of about 0.5 mm, and a gold wire was also bonded by a graphite paste. After that, an about 0.2-mm-thick resin coating intended to reduce elimination of $H_2O$ was provided. Thus, the dielectric constant and impedance characteristics of the single crystal of a charge-separated ionic solid represented by formula (1) and formed of $[Au_4Co_2(dppe)_2(D-pen)_4]^{2+}$ and anions were examined by alternating-current impedance measurement using Solartron 1260 and Solartron 1296 manufactured by Solartron Analytical. The probe used in the measurement was installed in a refrigerant-free refrigerating machine manufactured by IWATANI Corporation. The temperature dependence and frequency characteristics of the dielectric constant and impedance characteristics were examined using periodic voltages at frequencies from 100 Hz to 0.1 Hz in the temperature range from 100 K to 450 K.
(Result)

The results are shown in FIGS. 3 to 5. FIG. 3 shows the temperature dependence of the dielectric constant of $[Au_4Co_2(dppe)_2(D-pen)_4](Cl)_2 \cdot qH_2O$ as a compound representative of the dielectric property of the charge-separated ionic solid of the present invention. It was observed that the dielectric constant at 100 K is about 1.7, which is comparable to that of glass, and shows little frequency dependence, while in the temperature region above 320 K, mainly the dielectric constant ε' at 100 Hz or less abruptly increases, and the dielectric constant at 0.1 Hz reaches 70100 at 450 K.

FIG. 4 shows the temperature dependence of the dielectric loss of $[Au_4Co_2(dppe)_2(D-pen)_4](Cl)_2 \cdot qH_2O$ as a compound representative of the dielectric property of the charge-separated ionic solid of the present invention. It was observed that the dielectric loss, which is inversely proportional to the direct-current electrical resistance value, is small at 100 K but abruptly increases in the temperature region above 320 K.

The sensitivity of a resistive thermometer, which performs temperature measurement based on the correlation between temperature and resistance value, is determined by the precision of the detection system and the degree of temperature dependence of the resistance value. A CTR thermistor, which undergoes an abrupt decrease in resistance value with increasing temperature, preferably has the following property: the decrease in resistance value with increasing temperature is large. In order to illustrate the operation of the charge-separated ionic solid of the present invention in a thermometer or a CTR thermistor, FIG. 5 shows the temperature dependence of the alternating-current impedance at different frequencies for $[Au_4Co_2(dppe)_2(D-pen)_4](Cl)_2 \cdot qH_2O$ as a compound representative of the dielectric property of the charge-separated ionic solid of the present invention. It was observed that the alternating-current impedance at 0.1 Hz (1 V/mm) is initially about $10^{12} \Omega$ or more, then decreases continuously and abruptly, and becomes about $10^7 \Omega$ at 450 K. It was also observed that at 10 to 100 Hz, the alternating-current impedance continuously decreases to $\frac{1}{10^3}$ to $\frac{1}{10^4}$ with a temperature change from 100 K to 450 K. The continuity and amount of the temperature-dependent change in resistance value of the substance of the present invention are adequate for the use of this substance in a high-sensitive resistive thermometer. The rate of change in resistance is adequate for use in a CTR thermistor even when the temperature range is limited to a temperature range of 50 K over which a typical vanadium-based CTR thermistor operates.

(2) I-V Characteristics
(Method)

The method described in Example 6 was used to provide wiring on a single crystal of charge-separated ionic solid with a cross-sectional area of 0.7 mm×0.7 mm and a thickness of 0.5 mm, and the I-V characteristics of the single crystal of the charge-separated ionic solid represented by formula (1) and formed of $[Au_4Co_2(dppe)_2(D-pen)_4]^{2+}$ and anions were measured by using a FCE measurement apparatus manufactured by TOYO Corporation and sweeping the voltage frequency at a period from 0.1 Hz to 100 Hz.
(Result)

FIG. 6 shows the I-V characteristics measured at 420 K by sweeping the voltage frequency between ±100 V at a period of 0.1 Hz. As represented by the result shown in FIG. 6, I-V characteristics obeying the Ohm's law were invariably obtained in the voltage sweep between ±100 V or less in the range from 0.1 Hz to 100 Hz. FIG. 7 shows the I-V characteristics measured at 380 K by sweeping the voltage frequency between ±300 V at a period of 1 Hz. In the high-temperature, low-frequency, high-voltage region, behaviors deviating from the I-V characteristics were sometimes observed, whereas in the voltage sweep at 1 Hz or higher and between ±300 V or less, behaviors obeying the Ohm's law were observed. Such I-V characteristics of the charge-separated ionic solid of the present invention, coupled with the temperature dependence and frequency characteristics of the impedance characteristics which are shown in FIG. 5, enable the ionic solid to be used in a resistive thermometer even under conditions of alternating-current 100 V and 60 Hz or 50 Hz of household power supplies. Further, a large change in electrical resistivity occurs over a wide temperature region, and the use of a thermometer by direct-current driving, which yields the maximum sensitivity of the thermometer, does not cause any problem.

Example 8

(1) Electrostrictive Property (Evaluated from I-V Characteristics)
(Method)

An electrode was formed with a graphite paste on a single crystal of charge-separated ionic solid with a cross-sectional area of about 1 mm×1 mm and a thickness of about 0.8 mm, and a gold wire was also bonded by a graphite paste. After that, an about 0.2-mm-thick resin coating intended to reduce elimination of $H_2O$ was provided. Thus, the I-V characteristics of the single crystal of the charge-separated ionic solid represented by formula (1) and formed of $[Au_4Co_2(dppe)_2(D-pen)_4]^{2+}$ and anions were measured using a FCE measurement apparatus manufactured by TOYO Corporation. A heater and a thermometer attached to the measurement probe were used for temperature control and, at temperatures of 300 K, 380 K, and 420 K, the voltage was increased at a constant voltage sweep rate from 0 V to 400 V in 25 seconds, then from 400 V to −400 V in the next 50 seconds, and subsequently from −400 V to 0 V in 25 seconds. During this process, the current value I was measured to obtain I-V characteristic curves. Such a voltage change process will hereinafter be referred to as "voltage sweep at 10 mHz".
(Result)

The results are shown in FIGS. 8 to 10.

FIG. 8 shows the I-V characteristics measured by voltage sweep at 10 mHz at temperatures of 300 K, 380 K, and 420 K for $Au_4Co_2(dppe)_2(D\text{-pen})_4](NO_3)_2 \cdot qH_2O$ as a compound representative of the dielectric property of the charge-separated ionic solid of the present invention. As for the I-V characteristics at 300 K, I was lower than that at 380 K and 420 K, i.e., the resistance was high, and only a behavior obeying the Ohm's law was observed even in an extended voltage range. At 380 K, the I value was high, i.e., the resistance was low, and a double hysteresis behavior was observed. At 420 K, the double hysteresis behavior was more evident. For I-V characteristics, current value I characteristics obeying the Ohm's law are interpreted as indicating that the current is a true current corresponding to transfer of true charges, while, unlike the case of true current assumption, current value I characteristics showing oscillation between positive and negative values as a function of voltage sweep are interpreted as indicating that the current is a polarization current generated by polarization. The voltage dependence of polarization current (on the right of FIG. 8), which was obtained by determining the difference from the assumed true current value indicated by a solid line in the figure, presented a double hysteresis loop with its center at the point where the current value I is 0. This suggests that the hysteresis loop of the I-V characteristics may be attributed to the dielectric property of the substance of the present invention and that this substance may have a potential to exhibit an electrostrictive phenomenon in which the substance experiences great strain upon voltage application.

FIG. 9 shows the I-V characteristics measured by voltage sweep at 10 mHz at temperatures of 300 K, 380 K, and 420 K for $[Au_4Co_2(dppe)_2(D\text{-pen})_4](Cl)_2 \cdot qH_2O$ as a compound representative of the dielectric property of the charge-separated ionic solid of the present invention, and FIG. 10 shows comparison between $[Au_4Co_2(dppe)_2(D\text{-pen})_4](Cl)_2 \cdot qH_2O$ and $[Au_4Co_2(dppe)_2(D\text{-pen})_4](NO_3)_2 \cdot qH_2O$ at 420 K. Also for the I-V characteristics shown in FIG. 9 for $[Au_4Co_2(dppe)_2(D\text{-pen})_4](Cl)_2 \cdot qH_2O$, double hysteresis was observed at 380 K and at 420 K. The comparison shown in FIG. 10 between the $[Au_4Co_2(dppe)_2(D\text{-pen})_4](Cl)_2 \cdot qH_2O$ and $[Au_4Co_2(dppe)_2(D\text{-pen})_4](NO_3)_2 \cdot qH_2O$ at 420 K revealed that the I-V characteristics of the two substances are qualitatively identical although the obtained result was that the I value of the former substance was higher, i.e., the electrical resistance value of this substance was lower, as in the case of dielectric property and impedance characteristics.

(2) Electrostrictive Property (Evaluated by Observation with Atomic Force Microscope and Confocal Microscope)
(Method)

In order to measure voltage application-induced strain of $[Au_4Co_2(dppe)_2(D\text{-pen})_4](Cl)_2 \cdot qH_2O$ as a compound representative of the dielectric property of the charge-separated ionic solid of the present invention, an electrode was formed with a graphite paste on a single crystal of this substance with a cross-sectional area of about 1 mm×1 mm and a thickness of about 1 mm, then a gold wire was also bonded by a graphite paste and, after that, an about 0.2-mm-thick resin coating intended to reduce elimination of $H_2O$ was provided to prepare a sample capable of being subjected to voltage application and heating. A probe of an atomic force microscope (AFM) was placed on this sample, and voltage sweep up to 320 V was carried out at a frequency of 10 mHz while the displacement of the probe was measured. Additionally, a surface of a single crystal sample of the substance with a cross-sectional area of about 1 mm×1 mm and a thickness of about 1 mm, in particular one of the major opposite surfaces in the sample of the single crystal, was bonded by a graphite paste to a glass sheet coated with an ITO film. On the other of the opposite surfaces of the single crystal of the substance, an electrode was formed with a graphite paste, then a gold wire was also bonded by a graphite paste and, after that, a resin coating intended to reduce elimination of $H_2O$ was provided to prepare a sample capable of being subjected to voltage application and heating. A voltage was applied to this sample while the sample was observed with a confocal microscope.
(Result)

The results are shown in FIG. 11 and FIG. 12.

FIG. 11 shows the amount of displacement of the AFM probe during the voltage sweep at 10 mHz which was performed at 420 K up to 320 V for $[Au_4Co_2(dppe)_2(D\text{-pen})_4](Cl)_2 \cdot qH_2O$ as a compound representative of the electrostrictive property of the charge-separated ionic solid of the present invention. The value of the displacement of the AFM probe was negative, and the difference between the maximum and minimum of the displacement was 0.7 μm. Since the thickness of the crystal between the electrodes was 1 mm, the amount of the change, calculated as a shrinkage ratio, was 0.07%, which is considerably larger than 0.02 to 0.04% corresponding to the shrinkage ratio of lead zirconate titanate ($PbZr(TiO_4)$) which has been widely used as a typical dielectric material. In addition, the direction of the change is opposite to that in the case of lead zirconate titanate.

FIG. 12 shows the crystal of $[Au_4Co_2(dppe)_2(D\text{-pen})_4](Cl)_2 \cdot qH_2O$ as a compound representative of the electrostrictive property of the charge-separated ionic solid of the present invention, as observed with a confocal microscope during voltage application at 420 K. The crystal height along the red line in the figure is shown in a diagram presented below the image. In this measurement, the height direction of the crystal corresponded to the direction of the voltage application, and shrinkage was observed both in the height direction and in the plane direction orthogonal to the height direction. This indicates that the substance of the present invention isotropically shrinks in all directions upon voltage application and exhibits a behavior different from that in an existing electrostrictive phenomenon where a substance expands in the voltage application direction in proportion to the square of the voltage. That is, the observation result is an exemplary one demonstrating that the substance of the present invention behaves as an electrostrictive material different from existing materials.

The invention claimed is:

1. A dielectric material, comprising:
   a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closet packed structure.

2. The dielectric material according to claim 1, wherein the charge-separation type non-coulombic ionic solid is a charge-separation type non-coulombic ionic solid in which multinuclear complex cations each composed of two metal elements and two ligands are aggregated to form cation clusters, the cation clusters are arranged in a face-centered cube, and inorganic anions serving as counter anions are aggregated to form anion clusters in tetrahedral interstices of the face-centered cube.

3. The dielectric material according to claim 1, wherein the cation cluster is an $M^1M^2$ hexa- to deca-nuclear complex cation cluster in which an element ($M^1$) selected from the group consisting of elements of Group 10 and Group 11 and an element ($M^2$) selected from the group consisting of elements of Group 6, Group 9, and Group 13 are linked via two ligands ($X^1$ and $X^2$).

4. The dielectric material according to claim 1, wherein the charge-separation type non-coulombic ionic solid is a charge-separation type non-coulombic ionic solid of formula (1):

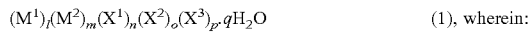   (1), wherein:

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^2$ represents a ligand having at least one thiol group and at least one carboxyl group;

$X^1$ represents an anion;

l and m each represent a number from 2 to 6, wherein a sum of l and m is 6 to 10; and n represents a number from 1 to 2, o represents a number from 2 to 6, and p and q each represent a number from 1 to 16.

5. The dielectric material according to claim 3, wherein $X^1$ is a ligand having at least two diarylphosphino groups.

6. The dielectric material according to claim 3, wherein $X^2$ is a ligand having a hydrogen-bonding functional group in addition to the at least one thiol group and the at least one carboxyl group.

7. The dielectric material according to claim 1, wherein the charge-separation type non-coulombic ionic solid undergoes a decrease in electrical resistance value to $\frac{1}{100,000}$ or less with a temperature change from 100 K to 450 K.

8. A thermometer, comprising:
the dielectric material according to claim 1.

9. A thermistor, comprising:
the dielectric material according to claim 1.

10. A device protection circuit configured to operate in response to temperature increase, the device protection circuit comprising a thermostat using the dielectric material according to claim 1.

11. An electrostrictive material comprising a charge-separation type non-coulombic ionic solid in which complex cations each composed of a metal element and a ligand are aggregated to form cation clusters, the cation clusters are arranged in a closest packed structure, and anions are aggregated to form anion clusters in interstices of the closest packed structure.

12. The electrostrictive material according to claim 11, wherein the charge-separation type non-coulombic ionic solid is a charge-separation type non-coulombic ionic solid in which multinuclear complex cations each composed of two metal elements and two ligands are aggregated to form cation clusters, the cation clusters are arranged in a face-centered cube, and inorganic anions serving as counter anions are aggregated to form anion clusters in tetrahedral interstices of the face-centered cube.

13. The electrostrictive material according to claim 11, wherein the cation cluster is an $M^1M^2$ hexa- to deca-nuclear complex cation cluster in which an element ($M^1$) selected from the group consisting of elements of Group 10 and Group 11 and an element ($M^2$) selected from the group consisting of elements of Group 6, Group 9, and Group 13 are linked via two ligands ($X^1$ and $X^2$).

14. The electrostrictive material according to claim 11, wherein the charge-separation type non-coulombic ionic solid is a charge-separation type non-coulombic ionic solid of formula (1):

   (1), wherein:

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^2$ represents a ligand having at least one thiol group and at least one carboxyl group;

$X^3$ represents an anion;

l and m each represent a number from 2 to 6, wherein a sum of l and m is 6 to 10; and n represents a number from 1 to 2, o represents a number from 2 to 6, and p and q each represent a number from 1 to 16.

15. The electrostrictive material according to claim 11, wherein $X^1$ is a ligand having at least two diarylphosphino groups.

16. The electrostrictive material according to claim 11, wherein $X^2$ is a ligand having a hydrogen-bonding functional group in addition to the at least one thiol group and the at least one carboxyl group.

17. The electrostrictive material according to claim 11, wherein the charge-separation type non-coulombic ionic solid isotropically shrinks upon voltage application.

18. An actuator comprising the electrostrictive material according to claim 11.

19. A multinuclear metal complex of formula (1a):

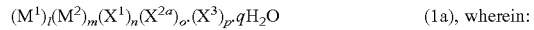   (1a), wherein:

$M^1$ represents an element selected from the group consisting of elements of Group 10 and Group 11;

$M^2$ represents an element selected from the group consisting of elements of Group 6, Group 9, and Group 13;

$X^1$ represents a ligand having at least two phosphino groups;

$X^{2a}$ represents a ligand having at least one thiol group and at least one carboxyl group, wherein the ligand is other than penicillamine;

$X^3$ represents an anion;

l and m each represent a number from 2 to 6, wherein a sum of l and m is 6 to 10; and n represents a number from 1 to 2, o represents a number from 3 to 6, and p and q each represent a number from 1 to 16.

20. The multinuclear metal complex according to claim 19, wherein $X^1$ is a ligand having at least two diarylphosphino groups.

21. The multinuclear metal complex according to claim 19, wherein $X^{2a}$ is a ligand having a hydrogen-bonding functional group in addition to the at least one thiol group and the at least one carboxyl group.

* * * * *